(12) United States Patent
Sein et al.

(10) Patent No.: US 10,457,890 B2
(45) Date of Patent: Oct. 29, 2019

(54) PHOSPHOLIPASE C

(71) Applicant: DSM IP ASSETS B.V., Heerlen (NL)

(72) Inventors: Arjen Sein, Echt (NL); Rene Marcel De Jong, Echt (NL); Evert Tjeerd Van Rij, Echt (NL); Willem Bijleveld, Echt (NL); Maarten Hotse Wilbrink, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/564,275

(22) PCT Filed: Apr. 8, 2016

(86) PCT No.: PCT/EP2016/057690
§ 371 (c)(1),
(2) Date: Oct. 4, 2017

(87) PCT Pub. No.: WO2016/162456
PCT Pub. Date: Oct. 13, 2016

(65) Prior Publication Data
US 2018/0134986 A1 May 17, 2018

(30) Foreign Application Priority Data

Apr. 9, 2015 (EP) .................................... 15162972

(51) Int. Cl.
C11B 3/00 (2006.01)
C12N 9/16 (2006.01)
C12P 7/64 (2006.01)
C12P 7/20 (2006.01)

(52) U.S. Cl.
CPC ............... *C11B 3/003* (2013.01); *C12N 9/16* (2013.01); *C12P 7/20* (2013.01); *C12P 7/64* (2013.01); *C12P 7/6445* (2013.01); *C12Y 301/04003* (2013.01)

(58) Field of Classification Search
None
See application file for complete search history.

(56) References Cited

FOREIGN PATENT DOCUMENTS

WO 2012/062817 A1 5/2012

OTHER PUBLICATIONS

Kubicek et al., "Comparative genome sequence analysis underscores mycoparasitism as the ancestral life style of Trichoderma."; Genome Bioliology, 2011:R40.1-R40, pp. 1-15. http://genomebiology.com/2011/12/4/R40.*
"Uniprot:G9MH09," (Feb. 22, 2012), XP055277672, pp. 1-10.
Lucas, S et. al., "EM_EST:FG382111," (May 22, 2008), XP055246415, pp. 6-9.
International Search Report in corresponding application No. PCT/EP2016/057690 dated Jun. 22, 2016.

* cited by examiner

*Primary Examiner* — Suzanne M Noakes
(74) *Attorney, Agent, or Firm* — McBee Moore Woodward & Vanik IP, LLC

(57) ABSTRACT

The present invention relates to a polypeptide having phospholipase C activity, selected from the group consisting of
i. a polypeptide comprising a mature polypeptide sequence of SEQ ID NO: 2;
ii. a polypeptide that has least 85%, 90%, 91%, 92%, 93%, 94%, 95%, 96%, 97%, 98% or 99% identity to the mature polypeptide sequence of SEQ ID NO: 2;
iii. a polypeptide encoded by a nucleic acid that hybridizes under medium stringency, preferably under high stringency conditions to the complementary strand of the mature polypeptide coding sequence of SEQ ID NO:1;
iv. a polypeptide encoded by a nucleic acid that has at least 85%, 90%, 91%, 92%, 93%, 94%, 95%, 96%, 97%, 98%, 99% or 100% identity to the mature polypeptide coding sequence of SEQ ID NO: 1.

A process for degumming a vegetable oil comprising contacting a vegetable oil comprising phospholipids with a polypeptide having phospholipase C activity of the invention or a composition of the invention, wherein phospholipids are hydrolyzed into diacylglycerol and phosphate ester and/or phosphate, separating the phosphate ester and/or phosphate from the vegetable oil wherein a degummed vegetable oil is obtained.

5 Claims, 1 Drawing Sheet
Specification includes a Sequence Listing.

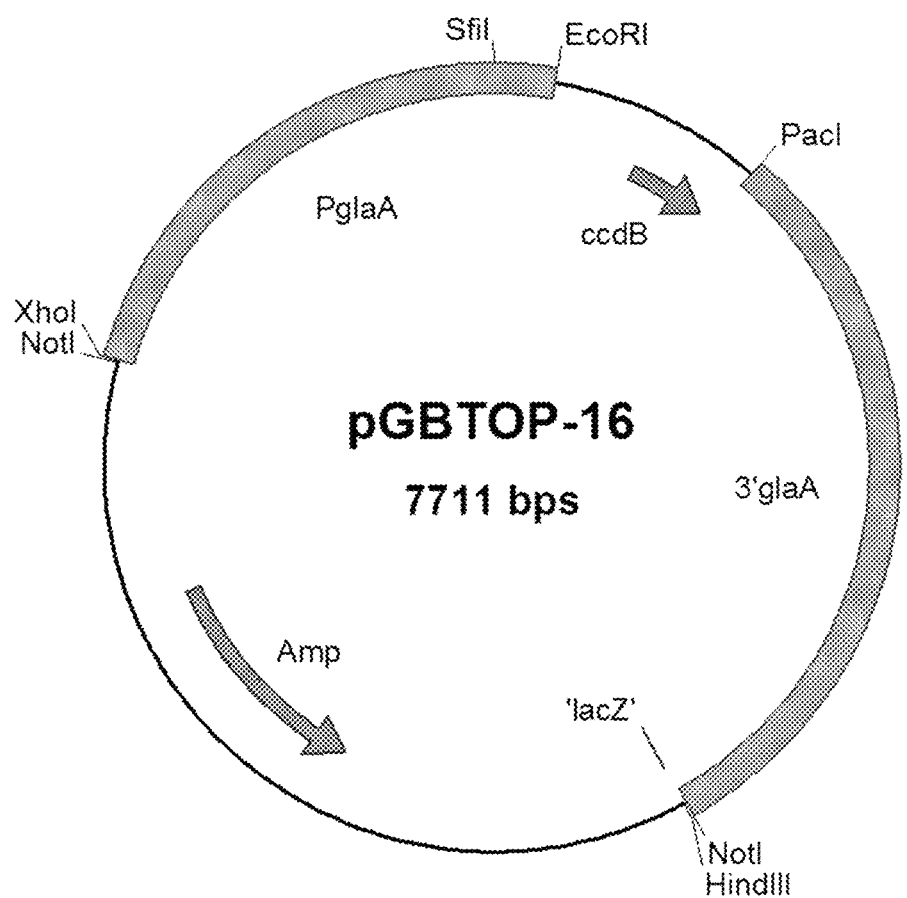

SEQUENCE LISTING

<160> NUMBER OF SEQ ID NOS: 4

<210> SEQ ID NO 1
<211> LENGTH: 1929
<212> TYPE: DNA
<213> ORGANISM: Artificial Sequence
<220> FEATURE:
<223> OTHER INFORMATION: CpO sequence phospholipase C of Hypocrea virens L061

<400> SEQUENCE: 1

```
atgcgccccg gctctgctct ctccctcctt gctcttggat ccgttgctca ggctgccatc      60
tccttggaag acagctctct ttctcctcgt gagattgaga acctcgagcg ttccatcgag     120
gctcgctctc ttgttgacga catctggaac gatatcaaga acgccgccac ctgcactgcc     180
tgccagggta tcctcgtcct cctcaagggt gttgccatct cggtgacga tgcgtttgtc      240 tccattgcca ctggtctttg caagctggcc aaggttgagg atgacgatgt ctgcgagggt     300
actgttgctc ttgaggctcc catcattgcc gatgccatcc gcaacatgga ccttggatcg     360
gatacttcca agctcttctg cggctctttc ctgggcctct gccccgagcc ttctgttcct     420
cagtggaaga tccccttccc cagcagcaag ccctccaccg gtcgtcccgc tcctagcggc     480
aagactcctc tcaaggtcgt ccagtactcc gacatccaca tcgaccctct gtacgtgtct     540
ggctccacca ccaactgcac caagcccgtc tgctgccgtc cctacactgc tgccgatgag     600
cctggtcaca gcacctcgcc tgctggtccc aacggtgacc acaagtgcga cacccccgtc     660
ggtctggaaa tatcaatgta ccaggccatc aagaacattg tccccgatgc tgccttgact     720
ctcttcaccg gcgacattgt cgaccacgct atctggaaca cctccaagcc ctacaaccag     780
aagcaaatct ccgatgccta cacctacatg agccagtacc tgggtctggt ctacggcact     840
gctggcaacc acgaagcgga ccctgccaac gccttccctc ccagtccat ctccaacagc      900 agccagtggg tgtacgatgc cctttctgct cagtggactc gctgggttgg tgcttctgct     960
gaggctcaga tcgagaacat cggtgcctac tcgaccaagt accccaacgg caacctgcgt    1020
atcatctccc tgaacaccaa cttctactac cgcatgaact tctggctata ccaggaagac    1080
attgagcagg accccgatgg ccagatcaag tggttggtgt ctgagctgga tgctgctgag    1140
aaggccggtg agcgtgtcta catcattggc cacatgccca tcggtgaatc ggatgctttc    1200
cacgctggaa gcaactacat cgaccaggtt gtcaaccgct actcttccac cattgctgcc    1260
atgttcttcg gtcacaccca cgttgaccac ttcgaggtca gctactccga ctactccaag    1320
caggatgcct cccacgccgt catggccagc tacatctgcc cctccctgac cccacctcc     1380 ggtatgcccct cttccgtgt ctacgatgtt gaccccgtga ccttcgccgt ccttgacacc    1440
accacctaca ttgccgacat gaccaacgcc aacttccaga ccactggtcc tgtctggacc    1500
```

-continued

```
aagctctact ctgccaagga agtctacggc tccaagctca accctcccgt gaccgacccc    1560
tccgctgagc tcaccccgc cttctggcac aacgtcaccg ctctcttcga gtccaactcc    1620
gccatgttca accagtacat ctccctcaag tcccgcggct ggaacgtcgc ctcctgcact    1680
ggtgactgcc agaagcagga gatctgccag ctccgtgctg ccgctccga gagcaactgc    1740 gttgttccca gccctggtct gcacatctcc aagcgctccg acgagcgtca cggacactct    1800
caccaccgtg ctcacgacca ccaggagtgc ggtatgagcg ctggtatgaa gaccattggc    1860
tccctggcca tgcgcaagga cctcctgaac gagctccagg tccgtgtcaa cgagctgcgc    1920
gccaaggcc                                                             1929
```

```
<210> SEQ ID NO 2
<211> LENGTH: 643
<212> TYPE: PRT
<213> ORGANISM: Hypocrea virens

<400> SEQUENCE: 2
```

```
Met Arg Pro Gly Ser Ala Leu Ser Leu Leu Ala Leu Gly Ser Val Ala
1               5                   10                  15

Gln Ala Ala Ile Ser Leu Glu Asp Ser Ser Leu Ser Pro Arg Glu Ile
                20                  25                  30

Glu Asn Leu Glu Arg Ser Ile Glu Ala Arg Ser Leu Val Asp Asp Ile
            35                  40                  45

Trp Asn Asp Ile Lys Asn Ala Ala Thr Cys Thr Ala Cys Gln Gly Ile
    50                  55                  60

Leu Val Leu Leu Lys Gly Val Ala Ile Phe Gly Asp Asp Ala Phe Val
65                  70                  75                  80

Ser Ile Ala Thr Gly Leu Cys Lys Leu Ala Lys Val Glu Asp Asp Asp
                85                  90                  95

Val Cys Glu Gly Thr Val Ala Leu Glu Ala Pro Ile Ile Ala Asp Ala
            100                 105                 110

Ile Arg Asn Met Asp Leu Gly Ser Asp Thr Ser Lys Leu Phe Cys Gly
        115                 120                 125

Ser Phe Leu Gly Leu Cys Pro Glu Pro Ser Val Pro Gln Trp Lys Ile
130                 135                 140

Pro Phe Pro Ser Ser Lys Pro Ser Thr Gly Arg Pro Ala Pro Ser Gly
145                 150                 155                 160

Lys Thr Pro Leu Lys Val Val Gln Tyr Ser Asp Ile His Ile Asp Pro
                165                 170                 175

Leu Tyr Val Ser Gly Ser Thr Thr Asn Cys Thr Lys Pro Val Cys Cys
            180                 185                 190

Arg Pro Tyr Thr Ala Ala Asp Glu Pro Gly His Ser Thr Ser Pro Ala
        195                 200                 205

Gly Pro Asn Gly Asp His Lys Cys Asp Thr Pro Val Gly Leu Glu Ile
    210                 215                 220

Ser Met Tyr Gln Ala Ile Lys Asn Ile Val Pro Asp Ala Ala Leu Thr
225                 230                 235                 240

Leu Phe Thr Gly Asp Ile Val Asp His Ala Ile Trp Asn Thr Ser Lys
                245                 250                 255

Pro Tyr Asn Gln Lys Gln Ile Ser Asp Ala Tyr Thr Tyr Met Ser Gln
            260                 265                 270

Tyr Leu Gly Leu Val Tyr Gly Thr Ala Gly Asn His Glu Ala Asp Pro
        275                 280                 285

Ala Asn Ala Phe Pro Pro Gln Ser Ile Ser Asn Ser Ser Gln Trp Val
```

```
                    290                 295                 300
Tyr Asp Ala Leu Ser Ala Gln Trp Thr Arg Trp Val Gly Ser Ala
305                 310                 315                 320
Glu Ala Gln Ile Glu Asn Ile Gly Ala Tyr Ser Thr Lys Tyr Pro Asn
                    325                 330                 335
Gly Asn Leu Arg Ile Ile Ser Leu Asn Thr Asn Phe Tyr Tyr Arg Met
                    340                 345                 350
Asn Phe Trp Leu Tyr Gln Glu Asp Ile Glu Gln Asp Pro Asp Gly Gln
                    355                 360                 365
Ile Lys Trp Leu Val Ser Glu Leu Asp Ala Ala Glu Lys Ala Gly Glu
                    370                 375                 380
Arg Val Tyr Ile Ile Gly His Met Pro Ile Gly Glu Ser Asp Ala Phe
385                 390                 395                 400
His Ala Gly Ser Asn Tyr Ile Asp Gln Val Val Asn Arg Tyr Ser Ser
                    405                 410                 415
Thr Ile Ala Ala Met Phe Phe Gly His Thr His Val Asp His Phe Glu
                    420                 425                 430
Val Ser Tyr Ser Asp Tyr Ser Lys Gln Asp Ala Ser His Ala Val Met
                    435                 440                 445
Ala Ser Tyr Ile Cys Pro Ser Leu Thr Pro Thr Ser Gly Met Pro Ser
450                 455                 460
Phe Arg Val Tyr Asp Val Asp Pro Val Thr Phe Ala Val Leu Asp Thr
465                 470                 475                 480
Thr Thr Tyr Ile Ala Asp Met Thr Asn Ala Asn Phe Gln Thr Thr Gly
                    485                 490                 495
Pro Val Trp Thr Lys Leu Tyr Ser Ala Lys Glu Val Tyr Gly Ser Lys
                    500                 505                 510
Leu Asn Pro Pro Val Thr Asp Pro Ser Ala Glu Leu Thr Pro Ala Phe
                    515                 520                 525
Trp His Asn Val Thr Ala Leu Phe Glu Ser Asn Ser Ala Met Phe Asn
                    530                 535                 540
Gln Tyr Ile Ser Leu Lys Ser Arg Gly Trp Asn Val Ala Ser Cys Thr
545                 550                 555                 560
Gly Asp Cys Gln Lys Gln Glu Ile Cys Gln Leu Arg Ala Gly Arg Ser
                    565                 570                 575
Glu Ser Asn Cys Val Val Pro Ser Pro Gly Leu His Ile Ser Lys Arg
                    580                 585                 590
Ser Asp Glu Arg His Gly His Ser His His Arg Ala His Asp His Gln
                    595                 600                 605
Glu Cys Gly Met Ser Ala Gly Met Lys Thr Ile Gly Ser Leu Ala Met
                    610                 615                 620
Arg Lys Asp Leu Leu Asn Glu Leu Gln Val Arg Val Asn Glu Leu Arg
625                 630                 635                 640
Ala Lys Ala

<210> SEQ ID NO 3
<211> LENGTH: 13
<212> TYPE: DNA
<213> ORGANISM: Artificial Sequence
<220> FEATURE:
<223> OTHER INFORMATION: translational initiation sequence of the
      glucoamylase glaA promoter

<400> SEQUENCE: 3
caccgtcaaa atg                                                        13
```

<210> SEQ ID NO 4
<211> LENGTH: 2145
<212> TYPE: DNA
<213> ORGANISM: Artificial Sequence
<220> FEATURE:
<223> OTHER INFORMATION: L061-insert artificial sequence

<400> SEQUENCE: 4

| | | | | | | |
|---|---|---|---|---|---|---|
| gaattcaagc | tagatgctaa | gcgatattgc | atggcaatat | gtgttgatgc | atgtgcttct | 60 |
| tccttcagct | tcccctcgtg | cagatgaggt | ttggctataa | attgaagtgg | ttggtcgggg | 120 |
| ttccgtgagg | ggctgaagtg | cttcctccct | tttagacgca | actgagagcc | tgagcttcat | 180 |
| ccccagcatc | attacaccgt | caaaatgcgc | cccggctctg | ctctctccct | ccttgctctt | 240 |
| ggatccgttg | ctcaggctgc | catctccttg | aagacagct | ctctttctcc | tcgtgagatt | 300 |
| gagaacctcg | agcgttccat | cgaggctcgc | tctcttgttg | acgacatctg | gaacgatatc | 360 |
| aagaacgccg | ccacctgcac | tgcctgccag | ggtatcctcg | tcctcctcaa | gggtgttgcc | 420 |
| atcttcggtg | acgatgcgtt | tgtctccatt | gccactggtc | tttgcaagct | ggccaaggtt | 480 |
| gaggatgacg | atgtctgcga | gggtactgtt | gctcttgagg | ctcccatcat | tgccgatgcc | 540 |
| atccgcaaca | tggaccttgg | atcggatact | tccaagctct | tctgcggctc | tttcctgggc | 600 |
| ctctgccccg | agccttctgt | tcctcagtgg | aagatcccct | tccccagcag | caagccctcc | 660 |
| accggtcgtc | ccgctcctag | cggcaagact | cctctcaagg | tcgtccagta | ctccgacatc | 720 |
| cacatcgacc | ctctgtacgt | gtctggctcc | accaccaact | gcaccaagcc | cgtctgctgc | 780 |
| cgtccctaca | ctgctgccga | tgagcctggt | cacagcacct | cgcctgctgg | tcccaacggt | 840 |
| gaccacaagt | gcgacacccc | cgtcggtctg | gaaatatcaa | tgtaccaggc | catcaagaac | 900 |
| attgtccccg | atgctgcctt | gactctcttc | accggcgaca | ttgtcgacca | cgctatctgg | 960 |
| aacacctcca | gcccctacaa | ccagaagcaa | atctccgatg | cctacaccta | catgagccag | 1020 |
| tacctgggtc | tggtctacgg | cactgctggc | aaccacgaag | cggaccctgc | caacgccttc | 1080 |
| cctcccagt | ccatctccaa | cagcagccag | tgggtgtacg | atgcccttc | tgctcagtgg | 1140 |
| actcgctggg | ttggtgcttc | tgctgaggct | cagatcgaga | acatcggtgc | ctactcgacc | 1200 |
| aagtaccccca | acggcaacct | gcgtatcatc | tccctgaaca | ccaacttcta | ctaccgcatg | 1260 |
| aacttctggc | tataccagga | agacattgag | caggaccccg | atggccagat | caagtggttg | 1320 |
| gtgtctgagc | tggatgctgc | tgagaaggcc | ggtgagcgtg | tctacatcat | tggccacatg | 1380 |
| cccatcggtg | aatcggatgc | tttccacgct | ggaagcaact | acatcgacca | ggttgtcaac | 1440 |
| cgctactctt | ccaccattgc | tgccatgttc | ttcggtcaca | cccacgttga | ccacttcgag | 1500 |
| gtcagctact | ccgactactc | caagcaggat | gcctcccacg | ccgtcatggc | cagctacatc | 1560 |
| tgcccctccc | tgaccccccac | ctccggtatg | ccctccttcc | gtgtctacga | tgttgacccc | 1620 |
| gtgaccttcg | ccgtccttga | caccaccacc | tacattgccg | acatgaccaa | cgccaacttc | 1680 |
| cagaccactg | gtcctgtctg | gaccaagctc | tactctgcca | aggaagtcta | cggctccaag | 1740 |
| ctcaaccctc | ccgtgaccga | cccctccgct | gagctcaccc | ccgccttctg | gcacaacgtc | 1800 |
| accgctctct | tcgagtccaa | ctccgccatg | ttcaaccagt | acatctccct | caagtcccgc | 1860 |
| ggctggaacg | tcgcctcctg | cactggtgac | tgccagaagc | aggagatctg | ccagctccgt | 1920 |

```
gctggccgct ccgagagcaa ctgcgttgtt cccagccctg gtctgcacat ctccaagcgc    1980
tccgacgagc gtcacggaca ctctcaccac cgtgctcacg accaccagga gtgcggtatg    2040
agcgctggta tgaagaccat tggctccctg gccatgcgca aggacctcct gaacgagctc    2100
caggtccgtg tcaacgagct gcgcgccaag gcctaaatta attaa                   2145
```

PHOSPHOLIPASE C

CROSS REFERENCE TO RELATED APPLICATIONS

This application is a National Stage entry of International Application No. PCT/EP2016/057690 filed 8 Apr. 2016, which claims priority to European Patent Application No. 15162972.2, filed 9 Apr. 2015.

BACKGROUND

The present invention relates to a polypeptide having phospholipase C activity and a process for degumming a vegetable oil.

DESCRIPTION OF RELATED ART

Phospholipases are a group of enzymes that catalyze the cleavage of phospholipids. There are several types of phospholipases. Phospholipase A1 (PLA1) removes the 1-position fatty acid from the phospholipid to produce a free fatty acid and a 1-lyso-2-acylphospholipid. Phospholipase B (PLB) hydrolyses both fatty acids leading to a glycerophosphate compound and two fatty acids, also known as lysophospholipase, and is considered an enzyme with a combination of both PLA1 and PLA2 activities. Phospholipase C (PLC) cleaves the glycerophosphate bond of phospholipids to produce a 1,2-diacylglycerol (DAG) and a phosphate or a phosphate ester (such as choline phosphate, ethanolamine phosphate and inositol phosphate). Phospholipase D (PLD) produces 1,2-diacylglycerophosphate, also known as phosphatidic acid, and a base group. Phospholipases are used amongst others in the refining or degumming of vegetable oils.

Traditionally, the degumming of vegetable oils is performed by hydrating the phospholipids in the oil by water, followed by separation of the phospholipids by for instance centrifugation. Alternatively also acid and/or caustic treatments may be used to optimize the separation. The removal of phospholipids causes substantial loss of oil during the refining of vegetable oils. The use of enzymatic treatment of phospholipids reduces the oil losses associated with traditional oil degumming methods. Phospholipase C (PLC) is in such separation particularly useful as it creates a diglyceride from the phospholipid, which adds to the neutral oil yield, and it breaks the emulsifying power of phospholipid, which results in less oil loss to the gum phase. Phospholipase A1 or A2, is compared to PLC less advantageous as it creates a lysophospholipid and a fatty acid. The latter still needs to be removed in an extra step further downstream in the refining process, and the lysophospholipid still has emulsifying power and will still absorb some neutral oil in the gum phase. Extended overviews of enzymatic oil degumming processes can be found in F. Galhardo and C. Dayton (2012), *Enzymatic Degumming*, in AOCS Lipid Library (lipidlibrary.aocs.org/processing/degum-enz/index.htm), and A. J. Dijkstra, 'Enzymatic degumming' in: Eur. J. Lipid Sci. Technol. 2010, 112, 1178-1189.

The major phospholipids in vegetable seed oils are phosphatidylcholine (PC), phosphatidylethanolamine (PE), phosphatidic acid (PA) and phosphatidyl inositol (PI). Depending on the affinity of phospholipases to any of the phospholipids, one or more phospholipases are needed for the efficient removal of phospholipids from vegetable oils. WO2008094847A1 discloses a process for degumming an oil composition wherein the oil composition is contacted simultaneously with a phospholipase C and phospholipase A, resulting in an increased reduction of phosphorus as compared to the use of either of the enzymes alone.

WO2011/046815 discloses the use of a combination of PLC (with high affinity for PC and PE) and phosphatidylinositol-specific PLC (PI-PLC) to obtain efficient phospholipid hydrolysis in an enzymatic oil degumming process.

WO2012/062817 discloses a phospholipase C enzyme from a strain *Kinochaeta* sp., which has activity towards the major phospholipids PC, PE, PA and PI.

An alternative phospholipase C which shows activity towards the phospholipids PC, PE, PA and PI from *Penicillium emersonii* is disclosed in WO2014/090161.

There is a need for a further phospholipase C enzyme which efficiently hydrolyses all major the phospholipids PC, PE, PA and PI

SUMMARY

The present invention relates to a polypeptide having phospholipase C activity, selected from the group consisting of i. a polypeptide comprising a mature polypeptide sequence of SEQ ID NO: 2;

ii. a polypeptide that has 80%, 85%, 90%, 91%, 92%, 93%, 94%, 95%, 96%, 97%, 98% or 99% identity to the mature polypeptide sequence of SEQ ID NO: 2;

iii. a polypeptide encoded by a nucleic acid that hybridizes under medium stringency, preferably under high stringency conditions to the complementary strand of the mature polypeptide coding sequence of SEQ ID NO:1;

iv. a polypeptide encoded by a nucleic acid that has at least 80%, 85%, 90%, 91%, 92%, 93%, 94%, 95%, 96%, 97%, 98%, 99% or 100% identity to the mature polypeptide coding sequence of SEQ ID NO: 1.

A predicted polypeptide sequence according to SEQ ID NO: 2 was found in a public database wherein the polypeptide sequence was annotated as a sphingomyelin phosphodiesterase. Surprisingly, it was found that a polypeptide having a mature sequence of SEQ ID NO: 2 has a phospholipase C activity. Surprisingly, a polypeptide as disclosed herein having phospholipase C activity comprises activity towards all of the major phospholipids phosphatidyl choline, phosphatidyl ethanolamine, phosphatidyl inositol, phosphatidyl serine and/or phosphatidic acid at a broad temperature range up to 80° C. and at a broad pH range, such as between pH 3 and 9. Furthermore, it was found that a phospholipase C according to the present invention efficiently hydrolyses a phospholipid substrate. For instance, a phospholipase as disclosed herein hydrolyses at least 80% of a phospholipid substrate at a concentration of less than 50 mg phospholipase (active) enzyme protein per gram of phospholipid in 24 hours. Preferably less than 40, 30, 20 or 10 mg phospholipase (active) enzyme protein per gram of phospholipid, or less than 1 mg/g phospholipid is required to hydrolyse at least 80% of phospholipid substrate in 24 hours. These characteristics are advantageous in oil degumming processes.

In one aspect the present invention relates to a composition comprising a polypeptide as defined herein.

In another aspect the present invention relates to a nucleic acid encoding a polypeptide having phospholipase C activity, which has at least 80%, 85%, 90%, 95%, 96%, 97%, 98%, or 99% sequence identity to the mature polypeptide encoding sequence of SEQ ID NO: 1. A nucleic acid as disclosed herein may comprise or may be SEQ ID NO: 1.

In yet another aspect the present invention relates to an expression vector comprising a nucleic acid as defined herein operably linked to one or more control sequence(s) that direct expression of the polypeptide in a host cell.

In other aspects the present invention relates to a recombinant host cell comprising a nucleic acid or an expression vector as defined herein and a method for preparing a polypeptide having phospholipase C activity comprising cultivating a host cell as defined herein in a suitable fermentation medium, under conditions that allow expression of the polypeptide, and preparing the polypeptide.

In yet another aspect the present invention relates to a process for hydrolysing phospholipids comprising incubating the phospholipids with a polypeptide having phospholipase C activity, or with a composition comprising a polypeptide as disclosed herein, wherein the phospholipids are hydrolysed.

In another aspect the present invention relates to a process for degumming a vegetable oil comprising contacting a vegetable oil comprising one or more phospholipids with a polypeptide having phospholipase C activity as disclosed herein or a composition comprising a polypeptide having phospholipase C activity as disclosed herein, wherein the one or more phospholipids are hydrolysed into diacylglycerol and phosphate ester and/or phosphate, separating the phosphate ester and/or phosphate from the vegetable oil wherein a degummed vegetable oil is obtained Definitions The term "complementary strand" can be used interchangeably with the term "complement". The complement of a nucleic acid strand can be the complement of a coding strand or the complement of a non-coding strand. When referring to double-stranded nucleic acids, the complement of a nucleic acid encoding a polypeptide refers to the complementary strand of the strand encoding the amino acid sequence or to any nucleic acid molecule containing the same.

The term "control sequence" can be used interchangeably with the term "expression-regulating nucleic acid sequence". The term as used herein refers to nucleic acid sequences necessary for and/or affecting the expression of an operably linked coding sequence in a particular host organism or in vitro. When two nucleic acid sequences are operably linked, they will usually be in the same orientation and also in the same reading frame. They will usually be essentially contiguous, although this may not be required. The expression-regulating nucleic acid sequences, such as inter alia appropriate transcription initiation, termination, promoter, leader, signal peptide, propeptide, prepropeptide, or enhancer sequences; Shine-Dalgarno sequence, repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either endogenous or heterologous to a host cell. Each control sequence may be native or foreign to the nucleic acid sequence encoding the polypeptide. When desired, the control sequence may be provided with linkers for the purpose of introducing specific restriction sites facilitating ligation of the control sequences with the coding region of the nucleic acid sequence encoding a polypeptide. Control sequences may be optimized to their specific purpose.

As used herein, the term "endogenous" refers to a nucleic acid or amino acid sequence naturally occurring in a host.

The term "expression" includes any step involved in the production of the polypeptide including, but not limited to transcription, post transcriptional modification, translation, post-translational modification, and secretion.

An "expression vector" comprises a polynucleotide coding for a polypeptide, operably linked to the appropriate control sequences (such as a promoter, and transcriptional and translational stop signals) for expression and/or translation in vitro, or in the host cell of the polynucleotide. The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e. a vector which exists as an extra-chromosomal entity, the replication of which is independent of chromosomal replication, e.g., a plasmid, an extra-chromosomal element, a mini-chromosome, or an artificial chromosome. Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. The vector system may be a single vector or plasmid or two or more vectors or plasmids, which together contain the total DNA to be introduced into the genome of the host cell, or a transposon.

A "host cell" as defined herein is an organism suitable for genetic manipulation and one which may be cultured at cell densities useful for industrial production of a target product, such as a polypeptide according to the present invention. A host cell may be a host cell found in nature or a host cell derived from a parent host cell after genetic manipulation or classical mutagenesis. Advantageously, a host cell is a recombinant host cell. A host cell may be a prokaryotic, archaebacterial or eukaryotic host cell. A prokaryotic host cell may be, but is not limited to, a bacterial host cell. A eukaryotic host cell may be, but is not limited to, a yeast, a fungus, an amoeba, an algae, a plant, an animal, or an insect host cell.

The term "heterologous" as used herein refers to nucleic acid or amino acid sequences not naturally occurring in a host cell. In other words, the nucleic acid or amino acid sequence is not identical to that naturally found in the host cell.

The term "hybridization" means the pairing of substantially complementary strands of oligomeric compounds, such as nucleic acid compounds. Hybridization may be performed under low, medium or high stringency conditions. Low stringency hybridization conditions comprise hybridizing in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency hybridization conditions comprise hybridizing in 6×SSC at about 45° C., followed by one or more washes in 0.2×SSC, 0.1% SDS at 60° C., and high stringency hybridization conditions comprise hybridizing in 6×SSC at about 45° C., followed by one or more washes in 0.2×SSC, 0.1% SDS at 65° C.

A "nucleic acid or polynucleotide sequence" is defined herein as a nucleotide polymer comprising at least 5 nucleotide or nucleic acid units. A nucleotide or nucleic acid refers to RNA and DNA. The terms "nucleic acid" and "polynucleotide sequence" are used interchangeably herein.

A "peptide" refers to a short chain of amino acid residues linked by a peptide (amide) bonds. The shortest peptide, a dipeptide, consists of 2 amino acids joined by a single peptide bond.

The term "polypeptide" refers to a molecule comprising amino acid residues linked by peptide bonds and containing more than five amino acid residues. The term "protein" as used herein is synonymous with the term "polypeptide" and may also refer to two or more polypeptides. Thus, the terms "protein" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity in the presence of a specific substrate under certain conditions may be referred to as enzymes. It will be understood that, as a result of the degeneracy of the genetic code, a multitude of nucleotide sequences encoding a given polypeptide may be produced.

An "isolated nucleic acid fragment" is a nucleic acid fragment that is not naturally occurring as a fragment and would not be found in the natural state.

The term "isolated polypeptide" as used herein means a polypeptide that is removed from at least one component, e.g. other polypeptide material, with which it is naturally associated. The isolated polypeptide may be free of any other impurities. The isolated polypeptide may be at least 50% pure, e.g., at least 60% pure, at least 70% pure, at least 75% pure, at least 80% pure, at least 85% pure, at least 80% pure, at least 90% pure, or at least 95% pure, 96%, 97%, 98%, 99%, 99.5%, 99.9% as determined by SDS-PAGE or any other analytical method suitable for this purpose and known to the person skilled in the art. An isolated polypeptide may be produced by a recombinant host cell.

A "mature polypeptide" is defined herein as a polypeptide in its final form and is obtained after translation of a mRNA into polypeptide and post-translational modifications of said polypeptide. Post-translational modification include N-terminal processing, C-terminal truncation, glycosylation, phosphorylation and removal of leader sequences such as signal peptides, propeptides and/or prepropeptides by cleavage.

A "mature polypeptide coding sequence" means a polynucleotide that encodes a mature polypeptide.

The term "nucleic acid construct" is herein referred to as a nucleic acid molecule, either single-or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

The term "promoter" is defined herein as a DNA sequence that binds RNA polymerase and directs the polymerase to the correct downstream transcriptional start site of a nucleic acid sequence to initiate transcription.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all. The term "recombinant" is synonymous with "genetically modified" and "transgenic".

"Sequence identity", or sequence homology are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl/). For protein sequences EBLOSUM62 is used for the substitution matrix. For nucleotide sequence, EDNAFULL is used. The optional parameters used are Needleman_Wunsch settings: Score*1, Matrix: BLOSUM62, a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, word length=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at DETAILED DESCRIPTION OF A PREFERRED EMBODIMENT.

The term "substantially pure" with regard to polypeptides refers to a polypeptide preparation which contains at the most 50% by weight of other polypeptide material. The polypeptides disclosed herein are preferably in a substantially pure form. In particular, it is preferred that the polypeptides disclosed herein are in "essentially pure form", i.e. that the polypeptide preparation is essentially free of other polypeptide material. Optionally, the polypeptide may also be essentially free of non-polypeptide material such as nucleic acids, lipids, media components, and the like. Herein, the term "substantially pure polypeptide" is synonymous with the terms "isolated polypeptide" and "polypeptide in isolated form". The term "substantially pure" with regard to polynucleotide refers to a polynucleotide preparation which contains at the most 50% by weight of other polynucleotide material. The polynucleotides disclosed herein are preferably in a substantially pure form. In particular, it is preferred that the polynucleotide disclosed herein are in "essentially pure form", i.e. that the polynucleotide preparation is essentially free of other polynucleotide material. Optionally, the polynucleotide may also be essentially free of non-polynucleotide material such as polypeptides, lipids, media components, and the like. Herein, the term "substantially pure polynucleotide" is synonymous with the terms "isolated polynucleotide" and "polynucleotide in isolated form".

A "synthetic molecule", such as a synthetic nucleic acid or a synthetic polypeptide is produced by in vitro chemical or enzymatic synthesis. It includes, but is not limited to, variant nucleic acids made with optimal codon usage for host organisms of choice.

A synthetic nucleic acid may be optimized for codon use, preferably according to the methods described in WO2006/077258 and/or WO2008000632, which are herein incorporated by reference. WO2008/000632 addresses codon-pair optimization. Codon-pair optimization is a method wherein the nucleotide sequences encoding a polypeptide that have been modified with respect to their codon-usage, in particular the codon-pairs that are used, are optimized to obtain improved expression of the nucleotide sequence encoding the polypeptide and/or improved production of the encoded polypeptide. Codon pairs are defined as a set of two subsequent triplets (codons) in a coding sequence. Those skilled in the art will know that the codon usage needs to be adapted depending on the host species, possibly resulting in variants with significant homology deviation from SEQ ID NO: 1, but still encoding the polypeptide according to the invention.

As used herein, the terms "variant", "derivative", "mutant" or "homologue" can be used interchangeably. They can refer to either polypeptides or nucleic acids. Variants include substitutions, insertions, deletions, truncations, transversions, and/or inversions, at one or more locations relative to a reference sequence. Variants can be made for example by site-saturation mutagenesis, scanning mutagenesis, insertional mutagenesis, random mutagenesis, site-directed mutagenesis, and directed-evolution, as well as various other recombination approaches known to a skilled person in the art. Variant genes of nucleic acids may be synthesized artificially by known techniques in the art.

FIGURES

FIG. 1: Schematic representation of the vector pGB-TOP16 used for cloning the phospholipase C gene.

DETAILED DESCRIPTION OF A PREFERRED EMBODIMENT

The present invention relates to a polypeptide having phospholipase C activity, selected from the group consisting of
i. a polypeptide comprising a mature polypeptide sequence of SEQ ID NO: 2;
ii. a polypeptide that has least 85%, 90%, 91%, 92%, 93%, 94%, 95%, 96%, 97%, 98% or 99% identity to the mature polypeptide sequence of SEQ ID NO: 2;
iii. a polypeptide encoded by a nucleic acid that hybridizes under medium stringency, preferably under high stringency conditions to the complementary strand of the mature polypeptide coding sequence of SEQ ID NO:1;
iv. a polypeptide encoded by a nucleic acid that has at least 85%, 90%, 91%, 92%, 93%, 94%, 95%, 96%, 97%, 98%, 99% or 100% identity to the mature polypeptide coding sequence of SEQ ID NO: 1.

Surprisingly, it was found that a polypeptide as defined herein having phospholipase C activity comprises activity towards all of the phospholipids phosphatidyl choline (PC), phosphatidyl ethanolamine (PE), phosphatidyl inositol (PI) and phosphatidic acid (PA). It is advantageous in oil degumming processes that a single phospholipase can be used to hydrolyse the major phospholipids instead of using a mixture of different phospholipases, such as phospholipase C, phosphatidyl-inositol specific (PI-PLC), or phospholipase A, which have activity on one or a selection of the major phospholipids PC, PE, PI or PA.

A polypeptide as disclosed herein has a pH optimum of about 4.5 to 5. For instance a pH optimum of a polypeptide having phospholipase C activity as disclosed herein may be determined by measuring phospholipase C activity in an aqueous solution comprising 100 mM acetate, 1% Triton X-100 and 1 mM $ZnSO_4$ with p-nitrophenyl phosphorylcholine (pNP-PC) as a substrate at 37° C.

Surprisingly, it was found that a polypeptide having phospholipase C activity as disclosed herein, more efficiently degraded phospholipids such as phosphatidyl choline (PC), phosphatidyl ethanolamine (PE), phosphatidyl inositol (PI) and phosphatidic acid (PA) in a neutral environment than in a more acid environment in a high oil/low water composition. A high oil/low water composition comprises less than 10, 8, 6, or 4 wt % of water relative to oil.

A polypeptide as disclosed herein may be an isolated, substantially pure, pure, recombinant, synthetic or variant polypeptide or a non-naturally occurring polypeptide.

A polypeptide having phospholipase C activity according to the present invention is advantageously derived from a *Hypocrea* sp., eg. *Hypocrea virens*. The wording "derived" or "derivable" from, with respect to the origin of a polypeptide as disclosed herein, means that when carrying out a BLAST search with a polypeptide according to the present invention, the polypeptide according to the present invention may be derivable from a natural source, such as a microbial cell, of which an endogenous polypeptide shows the highest percentage homology or identity with the polypeptide as disclosed herein.

In one embodiment, a polypeptide of the invention having phospholipase C activity is not a native polypeptide of Hypocrea virens containing a native leader sequence. For instance, a polypeptide of the invention having phospholipase C activity is not the complete amino acid sequence of SEQ ID NO: 2. For instance, a polypeptide of the invention having phospholipase C activity is not the amino acid sequence consisting of amino acids 1 to 643 of SEQ ID NO: 2.

A polypeptide having phospholipase C activity (EC 3.1.4.3) as disclosed herein is an enzyme that may hydrolyze phospholipids into diacylglyceride (DAG) and a phosphate from phosphatidic acid (PA), or DAG and a phosphate ester (from PC, PE and PI). Surprisingly, it was found that a polypeptide having phospholipase C activity according to the present invention has activity to the major phospholipids phosphatidyl choline, phosphatidyl ethanolamine, phosphatidyl inositol, and phosphatidic acid. An advantage of a polypeptide having activity to the major phospholipids is that only one phospholipase enzyme may be needed to hydrolyze all phospholipids into diglyceride and phosphate or phosphate ester, such as in a vegetable oil degumming process for efficient removal of phospholipids. A phospholipase as disclosed herein may have phosphatase activity E.C. 3.1.3. A phosphatase catalyzes the conversion of a phosphate ester, for instance the conversion of phosphate esters PC PE and PI into phosphate and choline, ethanol amine and inositol, respectively.

A polypeptide of SEQ ID NO: 2 comprises a leader sequence for secretion of the polypeptide outside cell. A leader sequence in SEQ ID NO: 2 may comprise amino acids 1 to 15, or 1 to 16, or 1 to 17, or 1 to 18 or 1 to 19, wherein the methionine (M) at position 1 is counted as 1.

A mature polypeptide sequence of SEQ ID NO: 2 as disclosed herein may comprise the amino acids from position 16, 17, 18, 19, or 20 to position 638, 639, 640, 641, 642 or 643 of SEQ ID NO: 2 wherein the methionine (M) at position 1 is counted as 1. For example a mature polypeptide of SEQ ID NO: 2 may comprise the amino acids from position 19 to position 643 of SEQ ID NO: 2, or is amino acids 19 to 643 of SEQ ID NO: 2, wherein the methionine (M) at position 1 is counted as 1. A polypeptide that has least 85%, 90%, 91%, 92%, 93%, 94%, 95%, 96%, 97%, 98% or 99% identity to the mature polypeptide sequence of SEQ ID NO: 2, may be a polypeptide that has at least 85%, 90%, 91%, 92%, 93%, 94%, 95%, 96%, 97%, 98% or 99% identity to amino acids 19 to 643 of SEQ ID NO: 2.

A polypeptide according to the present disclosure may advantageously be an isolated, substantially pure, pure, recombinant, synthetic or variant polypeptide of the polypeptide as defined herein. A polypeptide as disclosed herein may be purified. Purification of protein is known to a skilled person in the art, and may for instance comprise steps as separating proteins from cells or cell fractions, for instance by centrifugation, ammonium sulphate precipitation, ultracentrifugation, chromatography, or filtration, or ultrafiltration.

In one aspect the present disclosure relates to a composition comprising a polypeptide as disclosed herein. A composition as disclosed herein, may comprise a carrier, an excipient, an auxiliary enzyme, or other compounds. Typically a composition, or a formulation, comprises a compound with which a polypeptide having phospholipase C activity may be formulated. An excipient as used herein is an inactive substance formulated alongside with a polypeptide as disclosed herein, for instance sucrose or lactose, glycerol, sorbitol or sodium chloride. A composition comprising a polypeptide as disclosed herein may be a liquid composition or a solid composition. A liquid composition, typically an aqueous solution, usually comprises water. When formulated as a liquid composition, the composition usually comprises components that lower the water activity, such as glycerol, sorbitol or sodium chloride (NaCl). A solid composition comprising a polypeptide as disclosed herein may comprise a granulate comprising the enzyme or the composition comprises an encapsulated polypeptide in liquid matrices like liposomes or gels like alginate or carrageenans, or (synthetic.resins or silicas). There are many techniques known in the art to encapsulate or granulate a polypeptide or enzyme (see for instance G. M. H. Meesters, "Encapsulation of Enzymes and Peptides", Chapter 9, in N. J. Zuidam and V. A. Nedovid (eds.) "Encapsulation Technologies for Active Food Ingredients and food processing" 2010).

A composition as disclosed herein may also comprise a carrier comprising a polypeptide as disclosed herein. A polypeptide as disclosed herein may be bound or immobilized to a carrier by known technologies in the art, for instance by immobilizing the polypeptide on a carrier such as alginate or carrageenan. A composition as disclosed herein may also comprise an auxiliary enzyme, for instance a phospholipase A, or a PI-PLC. Alternatively, a composition as disclosed herein may comprise other enzymes that may be beneficial to enzyme assisted oil-degumming or refining. For instance a composition as disclosed herein may comprise one or more further enzyme(s) such as proteases, a chlorophyllases, pheophytinases, carbohydrases, for instance cell wall degrading enzymes such as cellulases, hemicellulases, pectinases and/or β-glucosidases, and/or lipases.

A composition comprising a polypeptide having phospholipase C activity as disclosed herein may also be a fermentation broth comprising the polypeptide. A composition may comprise a polypeptide having phospholipase C activity wherein the polypeptide is bound to cells or cell material. Alternatively, cells or cell material have been removed from the fermentation broth by centrifugation. Optionally, cells are killed for instance by a heating step.

The present invention also relates to a process for preparing a composition comprising a polypeptide as disclosed herein, which may comprise spray drying a fermentation medium comprising the polypeptide, or granulating, or encapsulating a polypeptide as disclosed herein, and preparing the composition. Spray drying is known to a skilled person and usually comprises producing a dry powder from a liquid or slurry comprising a polypeptide as disclosed herein by rapidly drying with hot gas.

In another embodiment the present invention relates to a nucleic acid encoding a polypeptide having phospholipase C activity as disclosed herein, which has at least 85%, 90%, 95%, 96%, 97%, 98%, or 99% sequence identity to SEQ ID NO: 1 or to the mature polypeptide encoding sequence of SEQ ID NO: 1.

A nucleic acid of the present disclosure may be an isolated, substantially pure, pure, recombinant, synthetic or variant nucleic acid of the nucleic acid or a non-naturally occurring nucleic acid. A polynucleotide sequence as disclosed herein may comprise SEQ ID NO: 1, or may comprise the mature polypeptide encoding sequence of SEQ ID NO:1.

In one other embodiment of the present invention a nucleic acid is disclosed that is an isolated, substantially pure, pure, recombinant, synthetic or variant nucleic acid of the nucleic acid of SEQ ID NO: 1. A variant nucleic acid sequence may for instance have at least 80% sequence identity to SEQ ID NO:1.

In another aspect, the present invention relates to an expression vector comprising a nucleic acid as disclosed herein operably linked to one or more control sequence(s) that direct expression of the polypeptide in an expression host cell.

An expression vector may be obtained for instance by inserting a nucleic acid of the present invention into an empty construct or vector. There are several ways of inserting a nucleic acid into a nucleic acid construct or an expression vector which are known to a skilled person in the art, see for instance Sambrook & Russell, *Molecular Cloning: A Laboratory Manual*, 3rd Ed., CSHL Press, Cold Spring Harbor, N.Y., 2001. It may be desirable to manipulate a nucleic acid encoding a polypeptide of the present invention with suitable control sequences. For instance the one or more control sequence(s) in an expression vector as disclosed herein may comprise a promoter sequence, a terminator sequence, and/or a leader sequence.

A promoter may be any appropriate promoter sequence suitable for a eukaryotic or prokaryotic host cell, which shows transcriptional activity, including mutant, truncated, and hybrid promoters, and may be obtained from polynucleotides encoding extracellular or intracellular polypeptides either endogenous (native) or heterologous (foreign) to the cell. The promoter may be a constitutive or inducible promoter. Preferably, the promoter is an inducible promoter, for instance a starch inducible promoter. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *Aspergillus* gpdA promoter, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof.

Any terminator which is functional in a cell as disclosed herein may be used, which are known to a skilled person in the art. Examples of suitable terminator sequences in filamentous fungi include terminator sequences of a filamentous fungal gene, such as from *Aspergillus* genes, for instance from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

In another embodiment the present invention relates to a recombinant host cell comprising a nucleic acid or an expression vector as disclosed herein. A suitable host cell may be a mammalian, insect, plant, fungal, or algal cell, or a bacterial cell. A suitable bacterial cell may be from the genera *Bacillus*, *Streptomyces* or *Pseudomonas*, for instance from the species *B. amyloliquefaciens*, *B. licheformis*, *S. coelicolor*, or *P. putida*.

A suitable host cell may be a fungal cell, for instance from the genus *Acremonium*, *Aspergillus*, *Chrysosporium*, *Fusarium*, *Myceliophthora*, *Penicillium*, *Rasamsonia*, *Talaromyces*, *Thielavia*, *Trichoderma*, *Saccharomyces*, *Kluyveromyces*, *Pichia*, for instance *Aspergillus niger*, *Aspergillus awamori*, *Aspergillus foetidus*, *A. oryzae*, *A. sojae*, *Talaromyces emersonii*, *Rasamsonia emersonii* *Chrysosporium lucknowense*, *Fusarium oxysporum*, *Myceliophthora thermophila*, *Thielavia terrestris* or *Trichoderma reesei* or, *Saccharomyces cerevisiae*, *Kluyveromyces lactis*, *Pichia pastoris*. Preferably, a recombinant or transgenic host cell for expression of a phospholipase C as disclosed herein is an *Aspergillus niger*.

The host cell may be genetically modified with a nucleic acid construct or expression vector as disclosed herein with standard techniques known in the art, such as electroporation, protoplast transformation or conjugation for instance as disclosed in Sambrook & Russell, *Molecular Cloning: A Laboratory Manual*, 3rd Ed., CSHL Press, Cold Spring Harbor, N.Y., 2001.

In one aspect the present invention relates to a process for the production of a polypeptide as disclosed herein comprising cultivating a recombinant host cell as disclosed herein in a suitable fermentation medium under conditions conducive to the production of the polypeptide and producing the polypeptide. A skilled person in the art understands how to perform a process for the production of a polypeptide as disclosed herein depending on a host cell used, such as pH, temperature and composition of a fermentation medium. A suitable fermentation medium usually comprises nutrients such a nitrogen, a carbon source and other essential elements known to a skilled person in the art for cultivating a particular host cell.

Host cells can be cultivated in shake flasks, or in fermenters having a volume of 0.5 or 1 liter or larger to 10 to 100 or more cubic meters. Cultivation may be performed aerobically or anaerobically depending on the requirements of a host cell.

A process for preparing a polypeptide as disclosed herein may further comprise recovering the polypeptide from the fermentation medium. Recovering the polypeptide may comprise isolating the polypeptide. Recovering may be performed by known methods in the art for instance recovering may comprise filtration, ultrafiltration, microfiltration, centrifugation or chromatography.

In another aspect the present invention relates to a process for hydrolysing phospholipids comprising incubating the phospholipids with a polypeptide having phospholipase C activity as disclosed herein or a composition as disclosed herein, wherein the phospholipids are hydrolysed. Phospholipids that may be hydrolysed include phosphatidyl choline, phosphatidyl ethanolamine, phosphatidyl inositol, phosphatidic acid, and/or phosphatidyl serine. Phospholipids may be derived from a vegetable oil or a fat, for instance an animal derived fat such a dairy fat. Surprisingly, it was found that at least part of the phospholipids phosphatidyl choline, phosphatidyl ethanolamine, phosphatidyl inositol, phosphatidic acid and phosphatidyl serine were hydrolysed by a polypeptide having phospholipase C activity as disclosed herein.

A process for hydrolysing phospholipids may comprise a step wherein phospholipids are separated from an oil, for instance a vegetable oil, or from a fat, for instance a dairy fat, for instance by water degumming, resulting in phospholipid-containing gums and water-degummed oil; incubating the phospholipid-containing gums with a polypeptide having phospholipase C activity as disclosed herein, wherein phospholipids are hydrolysed. A neutral oil fraction is usually obtained upon hydrolysis of the phospholipids and can be separated from the phosphor-containing fraction. The neutral oil can be then be added to the water degummed oil, which increases the yield of the oil.

Incubating phospholipids with a polypeptide having phospholipase C activity may be performed at any suitable pH and temperature. A suitable pH may for instance be a pH of between 3 and 9, or a pH of between 4 and 8, or a pH of between 5 and 7, or a pH of between 6 and 8. A suitable temperature may be a temperature of between 20 and 80° C., for instance between 30 and 70° C., such as between 40 and 60° C. or between 45 and 55° C.

In another aspect the present invention relates to a process for degumming a vegetable oil comprising contacting a vegetable oil comprising one or more phospholipids with a polypeptide having phospholipase C activity as disclosed herein or a composition as disclosed herein, wherein the one or more phospholipids are hydrolysed into diacylglycerol and phosphate ester and/or phosphate, separating the phosphate ester and/or phosphate from the vegetable oil wherein a degummed vegetable oil is obtained. In a process for degumming as disclosed herein hydrolysing phospholipids means that at least part of the phospholipids is hydrolysed. For instance, at least a part of the phospholipids phosphatidyl choline, phosphatidyl ethanolamine, phosphatidyl inositol, phosphatidic acid and/or phosphatidyl serine is hydrolysed.

Degumming a vegetable oil in a process as disclosed herein comprises reducing the phosphorus content in the vegetable oil. Advantageously, the atomic phosphorus content is reduced to less than 50 ppm P, or less than 20 ppm P or less than 10, or less than 5 ppm P, or less than 2 ppm P. The phosphorus content can be measured by standard ICP methods (inductively coupled plasma).

A vegetable oil in a process according to the present disclosure may be a crude oil or a previously degummed oil by other means, for instance by water degumming. A vegetable oil may also be obtained by pressing oil seed (pressed oil or expeller), by hexane extraction of oil seed. A vegetable oil may for instance be canola oil, castor oil, coconut oil, corn oil, cotton oil palm oil, palm kernel oil, peanut oil, rapeseed oil, rice bran oil, soybean oil or sunflower oil.

A process for degumming a vegetable oil as disclosed herein may further comprise a step of separating the degummed vegetable oil from gums. Such separating may for instance be achieved by centrifugation.

Contacting a vegetable oil comprising phospholipids with a polypeptide having phospholipase C activity may be performed in any suitable way. A polypeptide having phospholipase C activity may be dissolved in an aqueous medium and brought into contact with the vegetable oil by mixing or stirring, for instance by high-shear mixing.

A process for degumming a vegetable oil may be carried out at a pH of between 3 and 9, or a pH between 4 and 8, or a pH between 5 and 7, or a pH between 4 and 6, or a pH of between 3 and 7. The pH can be adjusted by known methods in the art for instance by the addition of acids, such as citric or phosphoric acid, optionally subsequently or simultaneously adding caustic such as sodium hydroxide. Advantageously phospholipids are hydrolysed at an acid pH value, since when phospholipids are hydrated they are more easily hydrolysed.

The temperature at which a process for degumming is carried out may be between 20 and 90° C., or between 25 and 80° C., such as between 30 and 70° C., or between 40 and 60° C., for instance between 45 and 55° C., for instance at a temperature of between 50 and 90° C. It was found advantageous to carry out a process for degumming at an elevated temperature, because the removal of gums rich in phosphorous-containing compounds by centrifugation is mostly done at elevated temperatures, such as 80° C. If the enzyme-assisted hydrolysis of phospholipids is performed at elevated temperature such as between 70 and 90° C., the temperature of the oil does not need to be lowered after hexane extraction or pressing and before enzyme-assisted hydrolysis.

In one aspect the present invention relates to a degummed vegetable oil obtainable by a process as disclosed herein.

The following examples illustrate the invention.

EXAMPLES

Materials and Methods

Example 1. Cloning and Expression of Phospholipase C

A polypeptide of *Hypocrea virens* of SEQ ID NO: 2, (L061 sequence) comprises a signal sequence of 18 amino acids for efficient secretion in *Hypocrea virens*, and a deduced mature protein sequence of 625 amino acids.

A codon-adapted DNA sequence for expression of the protein in *Aspergillus niger* was designed containing additional restriction sites for subcloning in an *Aspergillus* expression vector. Codon adaptation was performed as described in WO2008/000632. The codon optimized DNA sequence for expression of the gene encoding the L061 protein of SEQ ID NO: 2 in *A. niger* is shown in SEQ ID NO: 1.

The translational initiation sequence of the glucoamylase glaA promoter was modified into 5'-CACCGTCAAA ATG-3' (SEQ ID NO:3) and an optimal translational termination sequence 5'-TAAA-3' was used in the generation of the expression constructs (as also detailed in WO2006/077258). A DNA fragment (SEQ ID NO: 4), containing a.o. part of the glucoamylase promoter and the PLC encoding genes, was synthesized completely, purified and digested with EcoRI and PacI.

The pGBTOP-16 vector (FIG. 1) was linearized by EcoRI/PacI digestion and the linearized vector fragment was subsequently purified by gel-extraction. The DNA fragments were cloned into the pGBTOP-16 vector and the resulting vector was named pGBTOPL061. Subsequently, *A. niger* GBA 306 was transformed with pGBTOPL061 in a co-transformation protocol with pGBAAS-4, with strain and methods as described in WO 2011/009700 and references therein, and selected on acetamide containing media and colony purified according to standard procedures. Transformation and selection was performed as described in WO 98/46772 and WO 99/32617. Strains containing the L061 gene were selected via PCR with primers amplifying the introduced L061 gene to verify presence of the pGB- TOPL061 expression cassette. A single transformant expressing NBL-L061 was selected, and further replica-plated to obtain a single strain inoculum.

Example 2. Fermentation of *A. niger* NBL-L061 Strain

Fresh *A. niger* NBL-L061 spores were prepared and used for generating sample material by cultivation of the strain in 24 deep well plates (Axygen, Union City, USA) containing 3 ml fermentation medium 2 (15% w/v maltose, 6% w/v bacto-soytone, 1.5% w/v $(NH_4)_2SO_4$, 0.1% w/v $NaH_2PO_4.H_2O$, 0.1% w/v $MgSO_4.7H_2O$, 0.1% w/v L-arginine, 8‰ w/v Tween-80, 2‰ w/v Basildon, 2% w/v MES, pH 5.1). The 24 deep well plates were covered with a Breathseal (Greiner bio-one, Frickenhausen, Germany) and a lid. After 6 days of growth at 34° C., 550 rpm and 80% humidity in a Microton incubator shaker (Infors AG, Bottmingen, Switzerland) 1.5 mL samples were taken, the mycelium was separated from the supernatant by centrifugation for 30 min at 4000 g and the supernatants were stored at −20° C. until further analyses.

Example 3. Activity Determination of Phospholipase L061

3.1. Phospholipase C (PLC) Activity Assay (for Screening)

The PLC activity of the samples L061 A5 and C5 was determined using the chromogenic substrate p-nitrophenyl phosphorylcholine (pNP-PC). The substrate solution consisted of 10 mM pNP-PC (Sigma N5879, Zwijndrecht, the Netherlands), 100 mM acetate buffer pH 5.0, 1% Triton X-100 and 1 mM $ZnSO_4$. A mixture of 20 μL sample and 180 μL substrate solution was incubated at 37° C. for 60 min. The reaction was stopped by adding 100 μL reaction mixture to 100 μL stop reagent containing 1 M TRIS and 50 mM EDTA adjusted to pH 10 with 2 M NaOH. A blank was made by adding the stop reagent before the enzyme sample. The optical density (OD) of samples and blanks were measured at 405 nm.

Calibration was performed by preparing pNP solutions of respectively 0-0.5-1.0-2.0-2.9-4.0 mM in above mentioned buffer. 20 μL of each standard solution was mixed with 180 μL substrate and 100 μL of the mixture was added to 100 μL stop reagent. The OD of each solution was measured at 405 nm. By using linear regression, the slope of the calibration line was calculated.

Activity was calculated by using the following formula:

$$U/mL = \frac{\Delta Abs \times Df}{t * slope}$$

$\Delta Abs = (A_{sample} - A_{blank})$
Df=dilution factor of sample
slope=slope of p-nitro-phenol calibration curve (mL/μmol)
t=incubation time assay (60 min)

One U is defined as the amount of enzyme that liberates 1 μmol p-nitrophenol per minute under the conditions of the test (pH 5, 37° C.).

3.2. Phospholipase C (PLC) Activity Assay (for General Activity Measurement)

The PLC activity of samples L061 SF1, SF2 and SF3 was determined as described under 3.1. with the exception that an acetate buffer with 0.2% Triton X-100 was used and a mixture of 40 μL sample* and 960 μL substrate solution was incubated at 37° C. for 30 min.

*The sample had been diluted in 100 mM acetate buffer pH 5.0 with 0.2% triton X-100 and 1.0 mM Zinc sulfate. After centrifugation, the supernatant was used for the activity assay. The sample was diluted in such a way that the ΔAbs is between 0.1 and 1.0.

Accordingly, calibration was performed by preparing pNP solutions in 1000 μl and incubation was performed for 30 min.

3.3. Protein Determination

Protein content was measured according the "Coomassie Plus protein kit" of Pierce (art. no. 23236).

See also internal method of analysis 2459—Universal Bradford protein assay using Coomassie Plus assay reagent, manual method.

Results of the PLC activity assays, protein determinations and specific activity are given in Table 2a and Table 2b

TABLE 1

Phospholipase C activity of different screening samples of *Hypocrea virens* gene codon optimized for and expressed in *Aspergillus niger*.

| Sample ID | OD 405 nm | Protein mg/ml | Activity U/ml | S.A. U/mg | Enzyme/g lecithin* mg/g | U/g |
|---|---|---|---|---|---|---|
| L061 A5 | 2.325 | 0.34 | 0.68 | 2.0 | 0.17 | 0.34 |
| L061 C5 | 2.899 | 0.12 | 0.87 | 7.2 | 0.06 | 0.44 |

TABLE 2

Phospholipase C activity of different samples of the *Hypocrea virens* gene codon optimized and expressed in *Aspergillus niger*.

| Sample ID | Protein Mg/ml | Activity U/ml | S.A. U/mg |
|---|---|---|---|
| L061 SF1 conc | 3.1 | 17.1 | 5.5 |
| L061 SF2 pure sup | | 0.06 | |
| L061 SF3 wh b* | 0.12 | 1.0* | 8 |

*Determined with SDS/PAGE, so only BS-PLC content

SF2 pure sup: supernatant from a shake flask production; SF1 conc is a concentrated version thereof; SF3 wh b is a third shake flask production, whole broth (without separation of the cell material from the supernatant.). Shake flask productions were done in 100 mL flasks with about 50 gram of material in the same way as described for the small scale sample.

Example 4. Determination of pH and Temperature Profile

The pH profile of phospholipase L061 was determined in a solution of 10 mM pNP-PC, 30 mM acetic acid, 30 mM MOPS, 30 mM MES, 0.2% triton X-100 and 1 mM $ZnSO_4$ adjusted with NaOH to a pH ranging from 4 to 7.5. Subsequently the same procedure as described in Example 3 was followed. A shake-flask-produced enzyme sample with an activity of 1.0 U/mL was used.

The temperature profile phospholipase L061 was determined using the method of Example 3 at different temperatures, using an enzyme sample prepared by a shake flask fermentation with an activity of 0.06 U/mL.

The results in Table 3 and Table 4 show that the mature phospholipase L061 according to SEQ ID NO: 2 has a pH optimum of about 5.0 and a temperature optimum of about 55° C.

TABLE 3 pH profile of phospholipase L061 (pH optimum is set at 100%)

| pH | relative activity (%) |
|---|---|
| 4.0 | 78.7 |
| 4.5 | 96.1 |
| 5.0 | 100.0 |
| 5.5 | 70.7 |
| 6.0 | 27.5 |
| 6.5 | 7.1 |
| 7.0 | 3.8 |
| 7.5 | 4.0 |

TABLE 4

Temperature profile of phospholipase L061 (temperature optimum is set at 100%)

| Temperature (° C.) | relative activity (%) |
|---|---|
| 20.1 | 14.3 |
| 30.1 | 33.4 |
| 37.2 | 56.0 |
| 43.9 | 80.6 |
| 47.8 | 93.7 |
| 52.0 | 96.4 |
| 55.0 | 100.0 |
| 60.1 | 73.9 |
| 65.0 | 29.7 |
| 69.8 | 7.0 |

Example 5. Hydrolysis of Phospholipids in a Dispersion of De-Oiled Lecithin in Water at pH 5 and 6 and 60° C.

5.1. General Method:

10 wt % of de-oiled lecithin [DOL, Lecisoya P97IP, Novastell, France] was dispersed in a buffer, a 10 mM citrate buffer for pH 4 and 10 mM phosphate buffer for pH 6, using an Silverson L4RT dispersing device, room temperature 3 minutes 8000 rpm (80% of maximum). This was brought to 37° C. and enzyme was added in 3, 4 or 5 wt %, the amount depending on the protein content. When the supernatant contained more than 1.0 mg protein/mL, only 3 wt % of the material was added to the DOL dispersion, for a level between 0.5 and 1.0 mg/mL 4 wt % was added, for a level below 0.5 mg/mL 5 wt % was added.

This dispersion was stirred at 37° C. or 60° C. for 24 hrs. After 4 and 24 hours a sample was taken. The sample was immediately heat treated to inactivate the enzyme by holding the sample for 5 minutes in a boiling water bath. Subsequently the samples were kept frozen until analysis by $^{31}P$ NMR.

5.2. $^{31}P$ NMR Method

For $^{31}P$ NMR 10 μL of 10% DOL dispersion was dispersed in 1 mL of an aqueous solvent containing demineralized water with 10% deuterium oxide (D$_2$O, Cambridge Isotope Laboratories, DLM-4), 25 mg/mL deoxycholic acid (Sigma D2510), 5.84 mg/mL EDTA di Na (Titriplex III, Merck 108418), and 5.45 mg/mL TRIS base (Tris(hydroxymethyl) aminomethane, Merck 108387), of which the pH was adjusted to pH 9 using 4N KOH and to which 2 mg/mL TIP internal standard (tri-isopropylphosphate, Aldrich 554669) (accurately weighed) was added.

All samples were measured in a Bruker 400 MHz AvanceIII NMR spectrometer with a Prodigy BBO probe. The temperature of the probe head was set at 300K.

The measurement for quantification was performed with semi-quantitative parameters: 128 scans, 90° pulse, D1=5 sec. Values are reported in μmol/g of dry weight (DOL) of the sample.

5.3. Incubation of L061 in a Dispersion of De-Oiled Lecithin at 60° C.

5 wt % of supernatant from sample L061 (*Hypocrea virens*; sample A5) was added to a DOL dispersion as described above, at pH 5 and 6. The DOL dispersion obtained after incubation for 24 hours and after inactivation of the enzyme was analysed by $^{31}P$ NMR. The $^{31}P$ NMR results are given in the following table, compared to the reference DOL dispersion kept for 24 hr at 60° C. at the same pH, in μmol/g and in mol % (free phosphate levels excluded from mol % calculations).

TABLE 5

Composition of de-oiled lecithin (DOL) incubated with L061 phospholipase at pH 5 and 6 at 60° C. for 24 hr.

| | | pH 5 and 6, 60° C. | | | | | | | |
|---|---|---|---|---|---|---|---|---|---|
| | | PL concentration in μmol/g | | | | PL amount in mol fraction | | | |
| | | pH 5 | | pH 6 | | pH 5 | | pH 6 | |
| | abbr | Ref | L061 | Ref | L061 | Ref | L061 | Ref | L061 |
| Phosphatidyl choline | PC | 0.83 | 0.03 | 0.70 | 0.03 | 0.39 | 0.06 | 0.38 | 0.04 |
| Choline phosphate | C-P | 0.01 | 0.19 | 0.01 | 0.29 | 0.00 | 0.34 | 0.00 | 0.40 |
| Phosphatidyl ethanolamine | PE | 0.61 | 0.09 | 0.53 | 0.09 | 0.28 | 0.17 | 0.28 | 0.12 |
| Ethanolamine phosphate | E-P | 0.21 | 0.08 | 0.01 | 0.09 | 0.00 | 0.13 | 0.00 | 0.12 |
| Phosphatidyl inositol | PI | 0.50 | 0.01 | 0.43 | 0.01 | 0.23 | 0.03 | 0.23 | 0.02 |
| Inositol phosphate | IP | 0.00 | 0.14 | 0.00 | 0.19 | 0.00 | 0.24 | 0.00 | 0.27 |
| Phosphatidic acid | PA | 0.21 | 0.02 | 0.19 | 0.03 | 0.10 | 0.03 | 0.10 | 0.04 |
| Free phosphate | PO4 | 0.04 | 0.16 | 0.16 | 0.27 | 0.02 | 0.29 | 0.09 | 0.37 |

The values in the table show that a phospholipase C L061 shows activity on PA, PC, PE and PI, at 60° C. and pH 5 and 6. Activity was also seen after 4 hours, after which hydrolysis had proceeded to 20-40% (values not reported).

Example 6. Hydrolysis of Phospholipids in Crude Soybean Oil at Neutral Conditions 100 gram crude soy bean oil (North American Expander, with about 2.16 wt % of total phospholipids—measured by NMR, see below) was brought to a temperature of 55° C. and first treated with 130 ppm NaOH (55° C. for 30 minutes), then 2.5% of water was added with enzyme obtained from shake flask fermentation (with 17.1 U/mL, see Example 3 above) at 3.14 µL/g oil. This corresponds to 2.5 U PLC per gram phospholipid At time points 0.5, 2, 4 and 24 hr a sample was taken and the composition of phosphorous compounds was analyzed by $^{31}$P NMR and diacylglyceride (DAG) levels by HPLC.

$^{31}$P NMR characterization was done in a slightly different protocol than as described in example 5.

In the present example the TIP/TMP internal standard solution was prepared by mixing 100 mM Triisopropyl phosphate (TIP, 97%, Aldrich, #554669) and Trimethylphosphate (TMP, 99+%, Aldrich, #241024) solutions in 2-propanol (IPA, HPLC grade, J. T. Baker, #9095-33) respectively, at a ratio of 1:1.

An extraction buffer was made with the same composition as the NMR solvent used for Example 5, except that the pH was brought to 10.5 using solid KOH. The extraction buffer was used to extract the phospholipids from the oil: An aliquot of ~220 µL of well stirred oil was weighed accurately into a 2 mL tube. 100 µL D$_2$O, and 900 µL extracting buffer were added to the tube. The sample was mixed at room temperature and 1400 rpm for 60 minutes (benchtop Eppendorf Thermomixer R). After 60 minutes, the sample was centrifuged in a benchtop Eppendorf 5417C centrifuge at 14000 rpm for 10 minutes. 600 µL of the aqueous extraction layer was transferred into a new tube, followed by accurate addition of 24 µL of the TIP/TMP standard solution to the sample. The mixture was mixed using a benchtop vortex for 15 seconds. 500 µL of this sample (accurately) was transferred into a clean NMR tube. NMR measurements were performed using a Bruker AVANCE™ 500 MHz NMR with QNP 500 MHz S2 5 mm probe with Z-gradient, using the $^{31}$P Channel at 202.4 Hz and proton decoupling. The temperature was set at 300K. The number of scans was typically set at 512, and a relaxation delay at 0.1 s.

Diacylglyceride levels were determined using a variant of the AOCS Official Method Cd 11d-96 by HPLC-ELSD, using an Agilent 1260 HPLC system with Agilent 380—ELSD and Agilent Prep-SIL Scalar HPLC column (4.6×150 mm, 10 µm particle size; part#443910-901). Materials: Chemicals EMD Hexanes, part#HX0290P-1, EMD Ethyl Acetate, part#EX0245P-1, EMD Isopropyl Alcohol (IPA), part#PX1838P-1, EMD formic acid 98-100%, part#1116701000, Sigma Aldrich 1,2-Dipalmitoyl-rac-glycerol, 99%, part#D2135-1G, Sigma Aldrich Glyceryl 1,3-dipalmitate, 99%, part#D1639-1G.

HPLC settings: Mobile phase A: Hexane/Mobile phase B: Hexane:Isopropanol:Ethyl Acetate:Formic Acid:800:100:100:1 and an elution gradient as follows:

| Time (min) | Mobile Phase A (%) | Mobile Phase B (%) |
|---|---|---|
| 0.00 | 98.0 | 2.0 |
| 5.50 | 65.0 | 35.0 |
| 7.50 | 2.0 | 98.0 |
| 10.00 | 2.0 | 98.0 |

Solvent Flow Rate: 2 mL/min, Operating Pressure: ~30 bar; Column temperature: 40.0° C.; Injection Volume: 5.00 µL Preparation of Oil Samples: An aliquot of 50 µL oil sample was brought into 2 mL HPLC vial, accurately weighed and subsequently 950 µL hexane/isopropanol (9:1) mixture was added to each oil sample. The sample was thoroughly mixed using a bench-top vortexer. This was measured against a standard from 1,2 DAG and 1,3 DAG in a 9:1 hexane:IPA mixture.

The results in Tables 6 and 7 show that the polypeptide of the present disclosure had activity towards all phospholipids PA, PE, PI and PC present in crude soy bean oil under neutral conditions. Table 8 shows that the 1,2 diacylglyceride production ran parallel with the breakdown of intact phospholipids. These results as well as the decrease of intact phospholipid levels show that a polypeptide having phospholipase C activity according to the present invention is capable of increasing the oil yield in an enzymatic degumming process under neutral conditions.

TABLE 6

Amount (in µM) of phospholipids, phosphate and phosphate esters in soybean oil incubated with phospholipase L061 versus time. PO$_4$ is the reaction product of the hydrolysis of PA. At t = 0 there is already some PO$_4$ present in the starting oil

| Time (h) | PA | PE | PI | PC | PO$_4$ | EP | IP | CP |
|---|---|---|---|---|---|---|---|---|
| 0 | 866 | 1496 | 1202 | 2153 | 301 | 0 | 0 | 0 |
| 0.5 | 739 | 1572 | 1072 | 1979 | 447 | 35 | 147 | 394 |
| 2 | 723 | 1649 | 792 | 1495 | 739 | 143 | 494 | 1069 |
| 4 | 587 | 1425 | 602 | 973 | 903 | 250 | 533 | 1356 |
| 24 | 238 | 636 | 429 | 106 | 1604 | 832 | 600 | 1998 |

TABLE 7

Amount of intact phospholipids in soybean oil incubated with phospholipase L061 versus time in mol %

| Time (h) | PA | PE | PI | PC |
|---|---|---|---|---|
| 0 | 100 | 100 | 100 | 100 |
| 0.5 | 85.3 | 105.1 | 89.2 | 91.9 |
| 2 | 83.5 | 110.2 | 65.9 | 69.5 |
| 4 | 67.8 | 95.3 | 50.1 | 45.2 |
| 24 | 27.5 | 42.5 | 35.7 | 4.9 |

TABLE 8

1,2-diacylglyceride and 1,3 diacylglyceride level in soybean oil incubated with phospholipase L061 in wt % versus time

| Time (h) | 1,2 DAG | 1,3 DAG |
|---|---|---|
| 0 | 0.25 | 0.15 |
| 0.5 | 0.4 | 0.16 |
| 2 | 0.74 | 0.17 |

TABLE 8-continued 1,2-diacylglyceride and 1,3 diacylglyceride level in soybean oil incubated with phospholipase L061 in wt % versus time

| Time (h) | 1,2 DAG | 1,3 DAG |
|---|---|---|
| 4 | 0.95 | 0.18 |
| 24 | 1.32 | 0.2 |

Example 7. Hydrolysis of Phospholipids in Crude Soybean Oil at Slightly Acidic Conditions A second reaction was run in the same way as described in the previous example, however now the oil was pretreated with 500 ppm citric and 138 ppm NaOH for acidic conditions and an enzyme concentration of 2.90 μL/g oil, which corresponds to 2.3 U/g phospholipid was added.

The results in Tables 9 and 10 show that the polypeptide having phospholipase according of the present disclosure had activity towards all phospholipids PA, PE, PI and PC present in crude soy bean oil under acid conditions. Table 11 shows that the 1,2 diacylglyceride production ran parallel with the breakdown of intact phospholipids.

TABLE 9

Amount (in μM) of phospholipids, phosphate and phosphate esters in soybean oil incubated with phospholipase L061 versus time

| Time (h) | PA | PE | PI | PC | PO4 | EP | IP | CP |
|---|---|---|---|---|---|---|---|---|
| 0 | 866 | 1496 | 1202 | 2153 | 301 | 0 | 0 | 0 |
| 0.5 | 884 | 1692 | 1170 | 2216 | 427 | 0 | 138 | 224 |
| 2 | 705 | 1356 | 758 | 1286 | 523 | 62 | 332 | 548 |
| 4 | 671 | 1234 | 708 | 990 | 631 | 131 | 354 | 749 |
| 24 | 375 | 818 | 587 | 341 | 1111 | 363 | 436 | 1313 |

TABLE 10

Amount (in mol %) of intact phospholipids in soybean oil incubated with phospholipase L061 versus time

| Time (h) | PA | PE | PI | PC |
|---|---|---|---|---|
| 0 | 100 | 100 | 100 | 100 |
| 0.5 | 102.1 | 113.1 | 97.4 | 103.0 |
| 2 | 81.4 | 90.6 | 63.1 | 59.7 |
| 4 | 77.5 | 82.5 | 58.9 | 46.0 |
| 24 | 43.3 | 54.7 | 48.9 | 15.8 |

TABLE 11

Diacylglyceride level (wt %) phospholipids in soybean oil incubated with phospholipase L061 versus time

| Time (h) | 1,2 DAG | 1,3 DAG |
|---|---|---|
| 0 | 0.25 | 0.15 |
| 0.5 | 0.33 | 0.17 |
| 2 | 0.53 | 0.16 |
| 4 | 0.64 | 0.16 |
| 24 | 0.91 | 0.21 |

The results in Example 6 and 7 show that a phospholipase of the present disclosure hydrolysed a higher amount of the phospholipids phosphatidyl choline, phosphatidyl ethanol amine, phosphatidyl inositol phosphatidic acid under neutral conditions than under acidic conditions.

Example 8. Hydrolysis of Phospholipids in Rape Seed Oil

Extracted rape seed oil from European origin (100 mL) was pretreated with 200 ppm NaOH, and directly after that 5% w/w enzyme was added, that was obtained from a shake flask fermentation by treating broth with 10 mg Triton/gram broth, 60 min at room temperature and 10 minutes centrifugation at 4,000 rpm. The sample was sheared by a Silverson high shear mixer (1 minute at full speed) and left to incubate well stirred at 60° C. for 24 hours. During incubation samples were drawn.

Samples were heat treated to inactivate the enzyme, frozen, freeze dried and treated with cold acetone to extract the polar lipids [10 mL acetone on 1 mL]. After drying the acetone precipitate was characterized by $^{31}$NMR as described in example 5. The results are shown in table 12 (for clarity the lysophospholipids and glycerophosphates compounds are left out).

TABLE 12

Phospholipid composition of extracted rapeseed oil incubated with phospholipase L061 versus time.

| Time [hr] | PC | C-P | PE | E-P | PI | I-P | PA | free PO$_4$ |
|---|---|---|---|---|---|---|---|---|
| | | | | μmol/g | | | | |
| 0 | 3.44 | 0.01 | 2.10 | 0.00 | 2.11 | 0.01 | 2.79 | 1.08 |
| 4 | 0.19 | 3.04 | 1.81 | 1.40 | 0.25 | 0.96 | 0.95 | 8.07 |
| 24 | 0.00 | 0.43 | 0.19 | 1.89 | 0.01 | 0.32 | 0.51 | 12.46 |
| | | | | mol % | | | | |
| 0 | 29.8 | 0.1 | 18.2 | 0.0 | 18.3 | 0.1 | 24.2 | 9.4 |
| 4 | 1.1 | 18.2 | 10.9 | 8.4 | 1.5 | 5.8 | 5.7 | 48.4 |
| 24 | 0.0 | 2.7 | 1.2 | 11.9 | 0.0 | 2.0 | 3.3 | 78.8 |

The results in Table 12 show that the enzyme can hydrolyze all phospholipids in rape seed oil.

Example 9. Hydrolysis of Dairy Phospholipids

Commercial dairy cream (Albert Heijn, Puur&Eerlijk) was freeze dried, washed with acetone to remove the nonpolar lipids, redispersed in water and 5% enzyme solution obtained as described in Exampl 8 was added. After 4 hr at 50° C. the sample was freeze dried.

This material was extracted with 3 ml CHCl$_3$/MeOH on 100 mg dry sample weight. After taking out the extract/solvent the residue was washed with 2 ml CHCl$_3$/MeOH, to yield the polar lipids and a part of the reaction products choline-phosphate, ethanolamine-phosphate, inositol phosphate and free phosphate (limited solubility in CHCl$_3$/MeOH). These portions of CHCl$_3$/MeOH were combined and dried under a stream of nitrogen. Subsequently the material was dissolved in the aqueous buffer and analyzed by $^{31}$P NMR as described above.

The results in Table 13 show that phospholipase C of the present disclosure hydrolyzes all phospholipids PC, PE, PI, PA and also phosphatidyl serine (PS).

TABLE 13

Amount of phospholipids and reaction products in extracted dairy cream after treatment with phospholipase of the present disclosure

|  | PC | C-P | PS | PE | E-P | PI | I-P | PA | total |
|---|---|---|---|---|---|---|---|---|---|
| In μmol/g | | | | | | | | | |
| Ref | 2.45 | 0.36 | 0.79 | 1.28 | 0.21 | 0.60 | 0.10 | 0.07 | |
| PLC treated | 0.06 | 2.62 | 0.00 | 0.14 | 3.21 | 0.02 | 0.19 | 0.03 | |
| In mol % | | | | | | | | | |
| Ref | 24.3 | 3.6 | 7.9 | 12.7 | 2.1 | 5.9 | 1.0 | 0.7 | 90.8 |
| PLC treated | 0.6 | 27.7 | 0.0 | 1.5 | 33.9 | 0.2 | 2.1 | 0.3 | 93.0 |

The invention claimed is:

1. A process for hydrolysing one or more phospholipids comprising:
   a) separating the one or more phospholipids from an oil;
   b) incubating the one or more phospholipids with a polypeptide having phospholipase C activity selected from the group consisting of:
      i) a polypeptide comprising a mature polypeptide sequence of SEQ ID NO: 2;
      ii) a polypeptide that has at least 85% sequence identity to the mature polypeptide sequence of SEQ ID NO: 2; and
      iii) a polypeptide encoded by a nucleic acid that has at least 85% sequence identity to the mature polypeptide coding sequence of SEQ ID NO: 1,
   wherein the one or more phospholipids are hydrolysed.

2. The process according to claim 1, wherein the one or more phospholipids comprise phosphatidyl choline, phosphatidyl ethanolamine, phosphatidyl inositol, phosphatidyl serine and/or phosphatidic acid.

3. A process for degumming a vegetable oil comprising:
   a) contacting a vegetable oil comprising one or more phospholipids with a polypeptide having phospholipase C activity or a composition thereof, wherein the one or more phospholipids are hydrolysed into diacylglycerol and phosphate ester and/or phosphate, and wherein the polypeptide having phospholipase C activity is selected from the group consisting of:
      i) a polypeptide comprising a mature polypeptide sequence of SEQ ID NO: 2;
      ii) a polypeptide that has at least 85% sequence identity to the mature polypeptide sequence of SEQ ID NO: 2; and
      iii) a polypeptide encoded by a nucleic acid that has at least 85% sequence identity to the mature polypeptide coding sequence of SEQ ID NO: 1; and
   b) separating the phosphate ester and/or phosphate from the vegetable oil wherein a degummed vegetable oil is obtained.

4. The process for degumming according to claim 3, wherein the one or more phospholipids are hydrolysed at a pH value of between 3 and 9.

5. The process according to claim 3, wherein the one or more phospholipids phosphatidyl choline, phosphatidyl ethanolamine, phosphatidyl inositol, phosphatidyl serine and/or phosphatidic acid are hydrolysed.

* * * * *